United States Patent [19]

Tinker et al.

[11] 4,268,688

[45] May 19, 1981

[54] ASYMMETRIC HYDROFORMYLATION PROCESS

[75] Inventors: Harold B. Tinker, Creve Couer; Arthur J. Solodar, St. Louis, both of Mo.

[73] Assignee: Monsanto Company, St. Louis, Mo.

[21] Appl. No.: 333,269

[22] Filed: Feb. 16, 1973

[51] Int. Cl.³ .............................................. C07C 45/50
[52] U.S. Cl. ..................... 560/177; 560/250; 560/254; 560/255; 560/266; 564/219; 564/342; 568/429; 568/451; 568/452; 546/237; 546/340
[58] Field of Search ......... 260/604 HF, 293.8, 297 R, 260/599, 488, 562 R, 570.9; 560/177, 250, 254, 255, 266; 568/429, 451, 452; 546/237, 340; 564/219, 342

[56] References Cited

U.S. PATENT DOCUMENTS

| | | | |
|---|---|---|---|
| 3,527,809 | 9/1970 | Pruett et al. | 260/602 R |
| 3,641,076 | 2/1972 | Booth | 260/604 HF |

FOREIGN PATENT DOCUMENTS 2132414  1/1973  Fed. Rep. of Germany .

OTHER PUBLICATIONS

C. Botteghi et al., Chimia, 26, No. 3, Mar. 1972, pp. 141–143.
JACS 94: 6429–6433, (1972), Kagan et al.

*Primary Examiner*—Norma S. Milestone
*Attorney, Agent, or Firm*—Herman O. Bauermeister; Joseph D. Kennedy

[57] ABSTRACT

This invention relates to a process for the preparation of optically active aldehydes by the asymmetric catalytic hydroformylation of olefins. The process comprises the hydroformylation of olefinically unsaturated prochiral compounds in the presence of an optically active coordination compound containing a metal which is selected from the group consisting of rhodium, iridium, and cobalt.

This invention describes a generalized process for the asymmetric hydroformylation of a wide variety of olefins in which a preponderance of one optical isomer is produced. It is especially useful for the preparation of natural products which may require the presence of only one optical isomer for their utilization, for example, as flavors, fragrances, and medications.

The catalyst systems for the process of this invention are formed in the presence of carbon monoxide and hydrogen, from coordination compounds consisting of a central metal atom, rhodium, iridium, or cobalt, and at least one optically active ligand, e.g., phosphine, arsine, stibine, or amine. The coordination compound may contain one or more additional ligands, which may be neutral or which may possess negative charges such as carbon monoxide, hydrogen, olefins and diolefins, and halides.

2 Claims, No Drawings

ASYMMETRIC HYDROFORMYLATION PROCESS

It has been discovered that a wide variety of olefinic compounds can be selectively hydroformylated in the presence of an optically active coordination compound to yield optically active compounds according to the following equation:

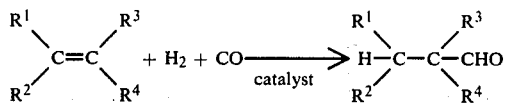

$R^1$, $R^2$, $R^3$, and $R^4$ are described in detail below. In the product of this reaction, one or both of the carbon atoms may be asymmetric or the molecule may be optically active due to molecular dissymmetry.

Frequently only one optical isomer is an effective medication, flavor, or fragrance. The other optical isomer may be innocuous and, consequently, need not be separated from the desired isomer. In these cases, the formation of a racemic mixture represents a 50% yield loss. However, in many instances, the presence of the undesired isomer is detrimental to the proper function of the medication, flavor, or fragrance and must be separated. The process of separation of optical isomers, i.e., resolution, is a very expensive and time consuming procedure. Usually the undesired optical isomer is destroyed resulting in a 50% loss in yield. In addition, the process of resolution rarely achieves a good recovery of the desired isomer and consequently results in an even greater yield loss. The separation of optical isomers is greatly facilitated when the desired isomer exists in an excess over its optical antipode. Consequently, a process for the preparation of an aldehyde which contains the desired optical isomer in excess over the other optical isomer represents a significant advancement in the state of the art.

The hydroformylation of optically inactive olefins as described in the prior art results in the synthesis of optically inactive compounds even when the hydroformylation reaction generates aldehydes or alcohols containing asymmetric carbon atoms or elements of molecular dissymmetry. The absence of optical activity in these products is the result of the formation of equal amounts of both optical isomers, i.e., a racemic mixture is formed.

The process of separating a racemic mixture into its optical components is called resolution. In general, resolution is a very inefficient, laborious, and time-consuming process. Frequently large yield losses are associated with this procedure.

Compounds are known as chiral compounds if they contain elements of molecular dissymmetry and/or one or more asymmetric carbon atoms but do not exhibit a molecular center, a plane of symmetry, or an alternating axis of symmetry. Chiral compounds can exist in two enantiomeric forms or mirror image forms also called optical isomers. Samples of chiral compounds which contain equal amounts of each enantiomorph are called racemic mixtures and are not optically active, i.e., they do not rotate plane polarized light. If a sample of a chiral compound contains definite but unequal portions of each enantiomorph, the sample is called partially racemic, partially resolved, or optically active. Resolved samples of a chiral compound containing only one enantiomer are called optically pure.

A prochiral compound is a compound which during a particular reaction is converted to a chiral compound. In the process of hydroformylation, a prochiral olefin is an olefin which is converted to a chiral aldehyde or alcohol. A specific example of a prochiral olefin is beta-methyl styrene:

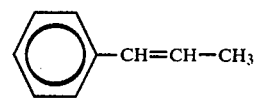

Other molecules which can be prochiral are compounds which, after hydroformylation, exhibit molecular dissymmetry rather than an asymmetric atom.

An achiral compound is a compound which is not chiral. For example, propionaldehyde (from the hydroformulation of ethylene) and n-butyraldehyde and iso-butyraldehyde (from the hydroformylation of propylene) are achiral compounds.

A recent comprehensive review of the techniques and the literature of asymmetric reactions (Asymmetric Organic Reactions by J. D. Morrison and H. S. Mosher, Prentice-Hall, Inc. 1971) does not mention any direct synthesis of optically active aldehydes. Indirect methods involving the conversion of optically active compounds, e.g., the reduction of optically active acids, or the oxidation of optically active alcohols or halides, can be employed. Unfortunately, such indirect routes require the prior resolution of the reactants (acid, alcohol, halide, etc.).

In contrast to the existing art, this invention describes a direct synthesis in good yields of optically active aldehydes. An additional benefit of the process of this invention is that the prior resolution of a stoichiometric quantity of one of the reactants into its optical isomers is not required. In essence, a prochiral olefin is converted into an optically active aldehyde without the use of optically active reactants. Resolution is limited to a component of the catalyst system which is not consumed during the reaction. One obvious advantage is that only a small (i.e. catalytic) quantity of optically active material must be prepared by resolution not the stoichiometric quantities typical of ether asymmetric reactions. Another advantage is that the optically active reagent is not consumed. Another advantage is that aldehydes can be synthesized directly from optically inactive reactants. Another advantage is that if resolution is necessary it can be accomplished much more efficiently since one of the optical isomers is present in excess over the other. Another advantage is that yield losses associated with the production of the undesired isomer can be substantially reduced.

Optically active hydroformylation is performed in the presence of a coordination complex of a metal selected from the group consisting of rhodium, iridium, and cobalt with optically active phosphine, arsine, stibine, or amine ligands of the formula $AR^5R^6R^7$ wherein A is phosphorus, arsenic, antimony, or nitrogen as described in detail later. The coordination complex may contain other ligands, for example, carbon monoxide, hydrogen, olefins and diolefins, and halides. The optically active ligand may also be a negatively charged ligand, for example, lactate and glutamate.

The coordination complex is represented by the formula $M(An)_w(olefin)_x(CO)_yL_z$ wherein M is a metal selected from the group consisting of rhodium, iridium, and cobalt; (An) is a coordinating or non-coordinating anion, such as halide, hydride lactate, acetate, or $B(C_6H_5)_4$; (olefin) is a mono or diolefin ligand such as ethylene, 1,5-cyclooctadiene, or norbornadiene; L is a neutral ligand most frequently optically active; and $w+x+y+z$ is 4,5, or 6. Examples of the coordination complexes of the present invention include $RhH(CO)$ (cyclohexylanisylmethyl phosphine)$_3$; Rh(1,5-cyclooctadiene (phenylanisylmethyl phosphine)$_2$ $B(C_6H_5)_4$, $Rh(CO)_3$ (cyclohexylanisymethyl phosphine)$_2$ $B(C_6H_5)_4$, and $Rh_4(CO)_{12}$(phenylmethylethylphosphine)$_8$.

It should be understood that the catalysts of this invention include not only the coordination complexes that contain two or three optically active ligands, as in the formulae $RhI(CO)(L^*)_2$, $Rh(CO)_2(L^*)_3(BPh_4)$, respectively, but also include those coordination complexes wherein the number of ligand-metal coodination bonds are described by the number of phosphorus, arsenic, antimony, or nitrogen atoms in the formulae wherein these atoms are provided by polydentate type ligands. For example, although there may be only one optically active ligand in a particular coordination complex, the formula $Rh(CO)_3(L^*)_2(BPh_4)$ still represents the complex of this invention if the optically active ligand is bidentate, i.e., it provides two coordination bonds. Likewise the formula $RhH(CO)(L^*)_3$ also represents a catalyst of the present invention wherein there is only one ligand present if that ligand is tridentate, i.e., it provides three coordination bonds.
(*indicates optical activity).

In the above metal coordination complex formulae, only one ligand (L*) need be optically active in order for the process of the invention to be operable. Although only one optically active group or ligand is required in the coordination complex it is preferred for ease of preparation of the complexes that all optically active ligands be the same.

It has also been found that good yields of optically active aldehydes can be achieved not only in the presence of the above described optically active coordination compounds which are coordination complexes of a metal selected from the group consisting of rhodium, iridium, and cobalt but can also be achieved when the hydroformylation is carried out in the presence of a catalyst that comprises a solution of a metal selected from the group consisting of rhodium, iridium, and cobalt and at least one equivalent of a phosphine and/or arsine ligand per mole of metal, provided that the ligand is optically active. For instance, the catalyst can be prepared by dissolving a soluble metal compound in a suitable solvent together with a ligand wherein the ratio of ligand to metal is at least one equivalent of ligand per mole of metal. Likewise, it has been found that the catalyst can be formed in situ by adding a soluble metal compound to the reaction mass together with the proper amount of optically active ligand to the reaction mass either before or during hydroformylation.

The preferred metal to be utilized is rhodium. Soluble rhodium compounds that can be utilized include rhodium trichloride hydrate, rhodium tribromide hydrate, rhodium sulfate, organic rhodium complexes with ethylene, propylene, etc., and diolefins such as 1,5-cyclooctadiene and 1,5-hexadiene, or an active form of metallic rhodium that is readily solubilized. Analogous iridium and cobalt compounds are also useful in this way.

Without prejudice to the present invention it is thought that the added complex is actually a catalyst precursor and that upon contact with hydrogen and carbon monoxide the complex is converted to an active form. This conversion can, of course, be carried out during the actual hydroformylation of the olefinic material or can be accomplished by subjecting the catalyst (or percursor) to hydrogen and carbon monoxide prior to addition to the olefin materials to be hydroformylated. The catalysts of the present invention preferentially hydroformylate and do not cause appreciable hydrogenation of the olefin feed or the aldehyde product.

In a preferred embodiment of this process an olefin is selectively hydroformylated in the presence of an optically active coordination rhodium, iridium, or cobalt complex according to the following equation:

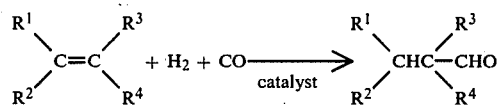

wherein $R^1$, $R^2$, $R^3$, and $R^4$ are each independently selected as discussed below and provided that the products of hydroformylation are chiral.

Optical activity of the metal coordination complex, according to the invention, resides in the phosphine, arsine, stibine, or amine ligands. This optical activity may result either from having three different groups on the phosphorus, arsenic, or antimony atom, or by having an optically active group attached to the phosphorus, arsenic, stibine, or nitrogen atom. In addition, such atoms can be optically active when they are part of a heterocyclic compound.

Catalyst precursors which may be used include, but are not limited to, coordination complexes containing ligands of the following formulae: $A^*R^5R^6R^7$ and $AR^{*5}R^6R^7$. In the formulae, an asterisk indicates asymmetry, and therefore optical activity. The asterisk denotes the symmetric atom or dissymmetric groups. As an example: R* indicates a dissymmetric group; A* indicates the phosphorus, arsenic, nitrogen, or antimony is asymmetric. In the ligand formula $A^*R^5R^6R^7$; $R^5$, $R^6$, and $R^7$ are each independently selected from the group consisting of hydrogen, alkyl or alkoxy, having at least one carbon atom and a maximum of 12 carbon atoms, substituted alkyl, said substitution selected from the group consisting of amino, carbonyl, aryl, nitro, and alkoxy, said alkoxy having a maximum of 4 carbon atoms, aryl, aryloxy, phenyl, substituted phenyl, said substitution selected from the group consisting of alkoxy and alkyl having a maximum of four carbon atoms, hydroxy, aryloxy, amino, and nitro, said substitution being less than 3 substituents, cycloalkyl having at least 3 carbon atoms, pyrryl, thienyl, furyl, pyridyl, piperidyl, menthyl, and 3-chlolesteryl.

If the optical activity of the ligand resides in an optically active group attached to the phosphorus, arsenic, antimony, or nitrogen atom, (formula AR*RR), there only has to be one such group, and the other two groups may be the same or inactive. In this instance, only one of the groups $R^5$, $R^6$, or $R^7$ has to be optically active, the remaining two groups may be identical and inactive.

Substituents on the phosphorus, arsenic, or antimony atoms include but are not limited to: methyl, ethyl, propyl, isopropyl, butyl and its isomers, pentyl and its isomers, hexyl and its isomers, heptyl and its isomers, octyl and its isomers, nonyl and its isomers, decyl and its isomers, undecyl and its isomers, dodecyl and its isomers, cyclopropyl, cyclobutyl, cyclopentyl, cyclohexyl, acetoxyphenyl, methylphenyl, ethylphenyl, propylphenyl, butylphenyl, dimethylphenyl, trimethylphenyl, hydroxyphenyl, phenoxyphenyl, anisyl, 3-cholesteryl, benzyl, pyrryl, furyl, pyridyl, thienyl, piperidyl, and menthyl.

A list of optically active phosphines, arsines, and stibines which may be utilized includes but is not limited to: methylethylphosphine, methylisopropylphosphine, ethylbutylphosphine, isopropylisobutylphosphine, methylphenylphosphine, ethylphenylphosphine, propylphenylphosphine, butylphenylphosphine, phenylbenzylphosphine, phenylbiphenylpyrrolephosphine, ethylisopropylisobutylphosphine, methylphenyl-4-methylphenylphosphine, ethylphenyl-4-methylphenylphosphine, methylisopropylphenylphosphine, ethylphenyl-2,4,5-trimethylphenylphosphine, phenylcyclopentylethylphosphine, cyclohexylmethylisopropylphosphine, 2,3-O-isopropylidine-2,3-dihydroxy-1,4-bis(-diphenylphosphino)butane, o-methoxyphenylmethylphenylphosphine, and the arsenic and antimony analogs of the above, such as methylethylarsine and methylisopropylstibine. Optically active amines which can be employed as ligands include amines with three R groups, one or all of which contain optically active centers such as alpha-phenylethylamine. In addition, nitrogen atoms which are members of heterocycles can also be optically active and consequently such amines, e.g. 1-azo-2-phenyl-bicyclo[2.2.2]octane, are effective ligands for the process of this invention.

The optically active aldehydes of the general formula

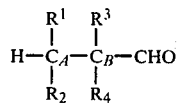

prepared in the practice of this invention are obtained by the hydroformylation of a prochiral olefin with the general formula

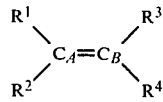

wherein $R^1$, $R^2$, $R^3$ and $R^4$ are subject to the following restrictions:

I $R^1$ is not identical to $R^2$; or
II $R^3$ is not identical to $R^4$. Furthermore,
III neither $R^1$ nor $R^2$ can be hydrogen; or
IV neither $R^3$ nor $R^4$ can be the formyl group (—CHO).

For the sake of clarity in this definition we have assumed that $R^1$ and $R^2$ are attached to the carbon atom ($C_A$) to which hydrogen is added and $R^3$ and $R^4$ are attached to the carbon atom ($C_B$) to which the formyl group is added during the hydroformylation reaction as depicted in the following equation:

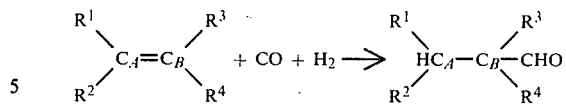

Prochiral olefins of this definition also include molecules of the above general formula where the R-groups are connected to form ring compounds, e.g., 3-methyl-1-cyclohexene.

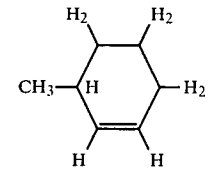

In addition $R^1$, $R^2$, $R^3$, and $R^4$ are each independently selected from the group consisting of (a) hydrogen (b) alkyl having at least one and a maximum of twenty-five carbon atoms (c) substituted alkyl said substitution being selected from the group consisting of amino, including alkylamino and dialkylamino such as benzylamino and dibenzylamino, hydroxy, alkoxy such as methoxy and ethoxy, acyloxy such as acetyoxy, halo, nitro, nitrile, thio, carbonyl, carboxamide, carboxaldehyde, carboxyl, carboxylic ester said ester having a maximum of ten carbon atoms (d) aryl including phenyl (c) substituted aryl including phenyl said substitution being selected from the group consisting of alkyl having a maximum of six carbon atoms, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester said ester having a maximum of ten carbon atoms, carbonyl, and, thio, said aryl substitution being less than four substituents (f) acyloxy such as acetoxy (g) alkoxy such as methoxy and ethoxy (h) amino including alkylamino and dialkylamino such as benzylamino and dibenzylamino (i) acylamino and diacylamino such as acetylbenzylamino and diacetylamino (j) nitro (k) carbonyl (l) nitrile (m) carboxyl (n) carboxamide (o) carboxaldehyde (p) carboxylic ester said ester having a maximum of 10 carbon atoms (q) alkylmercapto such as methylmercapto, provided that the compound after hydroformylation is chiral.

The reaction is conducted in the presence of a complex $M(An)_w(olefin)_x(CO)_y(L^*)_z$ where M is a metal selected from the group consisting of rhodium, iridium, and cobalt; (An) is a coordinating or noncoordinating anion; $L^*$ is an optically active ligand, and w,x,y, and z are whole numbers from 0 to 4, and $w+x+y+z$ is 4, 5, or 6.

The group $R^1$, $R^2$, $R^3$, and $R^4$ may also have an asymmetric carbon. This does not prevent the formation of an additional asymmetric carbon on hydroformylation.

It has also been found that excellent yields of optically active compounds can be achieved with those olefinic compounds wherein at least one of the $R^1$, $R^2$, $R^3$, or $R^4$ radicals is an oxygen containing group.

The hydroformylation reaction is usually conducted in a solvent, such as benzene, ethanol, toluene, cyclohexane, and mixtures of these solvents or in the olefin itself without a solvent. Aromatic or saturated alkane or cycloalkane solvents, which are unreactive under the hydroformylation conditions of this reaction, can be used. In the process for the asymmetric catalytic hydroformylation of olefins, the catalyst precursor is added to the solvent either as a compound per se or as its components which then form the catalyst in situ. When the catalyst is added as its components it may be added prior to, at the same time, or after the addition of the olefin. Components for the preparation of the catalyst in situ are the soluble metal compound and the phosphine, arsine, stibine, or amine ligands. The catalyst or catalyst percursor is added to the solution in the range of about $10^{-4}$ molar to about $10^{-1}$ molar.

In addition to the homogeneous reactions described in detail herein which involves a soluble metal complex as catalyst or catalyst precursor, in a homogeneous reaction system, the process of this invention is also carried out by employing a complex bound to a support (e.g., cross-linked polystyrene) which is not soluble in the solvent used for the reaction. In addition, an optically active complex on a support such as alumina is used in a vapor phase example of the process of this invention.

The pressure of the system will vary from about 1 atmosphere to about 150 atmospheres since it will be dependent upon the type of olefinic material, type of catalyst, size of apparatus, amount of components, and amount of solvent used. Lower pressures, including subatmospheric pressure, can be used as well as higher pressures.

Reaction temperatures may be in the range of about 25° C. to about 180° C. Higher temperatures may be used but are normally not required and may lead to an increase of side reactions and loss in selectivity to, and optical purity of, the product.

A preferred embodiment of the invention employs an excess of optically active ligand over that necessary to prepare the coordination complex. Molar excess of from about 1 to about 2000 can be employed depending on the initial concentration of the rhodium complex.

Upon completion of the reaction, the solvent is removed and the products and catalyst separated by conventional means, e.g., distillation or crystallization.

The following examples are illustrative only and the invention is not limited to them. In the examples, the % optical purity is determined by the following equation:

$$\% \begin{pmatrix} \text{optical} \\ \text{purity} \end{pmatrix} = \frac{\text{observed optical activity of the mixture} \times 100}{\text{optical activity of the pure enantiomorph}}$$

In the examples of this patent the optical rotation is determined employing a Perkin-Elmer 141 polarimeter using the Na 589 nanometer line. The concentration reported in the tables are g/100 ml of solution.

EXAMPLE 1

The preparation of levo-2,3-O-isopropylidene-2,3-dihydroxy-1,4-bis(diphenylphosphino)butane also designated as the (−) diop ligand employs the method of H. B. Kagan and T-P. Dang, *J. Amer. Chem. Soc.* 94, 6429 (1972). dextro-Diethyl tartrate is converted to the corresponding acetonide with acid and dimethoxypropane. The acetonide is reduced with LiAlH₄ to the corresponding diol acetonide which is reacted with toluene-sulfonyl chloride to give 1,4-ditosyl-2,3-O-isopropylidene-L-threitol. Reaction of this with sodium diphenylphosphide gives the desired ligand.

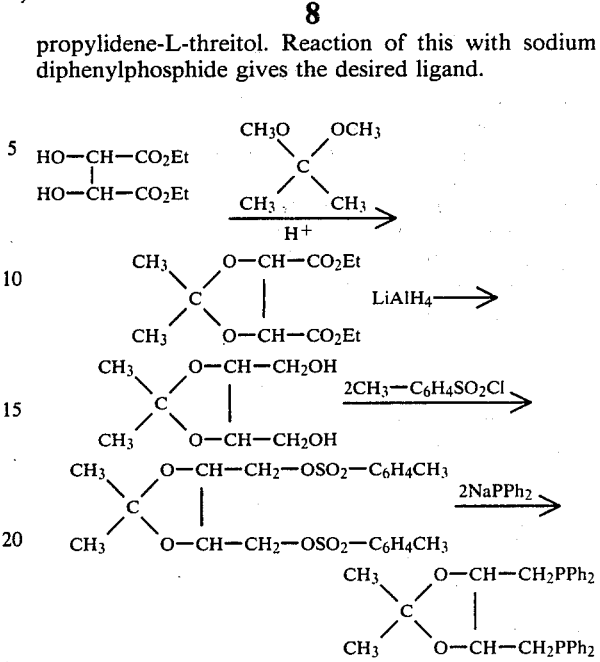

EXAMPLE 2

Rhodium norbornadiene levo-2,3-O-isopropylidene-2,3-dihydroxy-1,4-bis(diphenylphosphino)butane tetraphenylborate (Rh(NBD)diop BPh₄) is prepared as follows. [Rh(norbornadiene)Cl]₂ (285 mg) is slurried in 20 ml absolute MeOH under N₂ for 15 min. The ligand (levo-diop) (0.65 g) in 30 ml hot EtOH is added in one batch and the mixture stirred for 2 min. To the resulting clear solution is added 1.05 equivalents NaBPh₄ in EtOH and then 10 ml water. After stirring for 45 min. the mixture is filtered and the solids dried to give 1.1 g product.

Rhodium 1,5-cyclooctadiene levo-2,3-O-isopropylidene-2,3-dihydroxy-1,4-bis(diphenylphosphino)butane tetrafluoroborate (Rh(COD)(diop)BF₄) is prepared according to the following procedure. [Rh(1,5-cyclooctadiene)acetylacetonate] (155 mg) is slurried under N₂ with ligand, levo-diop, (259 mg) dissolved in 15 ml hot EtOH. After 10 min. the solution clears and 2.4 equivalents NaBF₄ in 11 ml 90% MeOH solution is added. After 5 min. stirring, 10 ml water is added. This is stirred an additional 30 min. and then filtered. The resulting solid is washed with water and dried to give 0.23 g product.

EXAMPLE 3

The optically active ligands CAMP (cyclohexylanisyl methylphosphine) and PAMP (phenylanisylmethylphosphine) are prepared according to the method described by Knowles, Sabacky, and Vineyard (*J. Chem. Soc., Chem. Comm.*, 10 (1972).

The preparation of Rh(COD)(CAMP)₂ BPh₄ is as follows: To a methanol solution (100 ml) in a nitrogen atmosphere containing CAMP(16.2 mmoles) is added 2.0 g of [Rh(COD)Cl]₂ (8.1 mmoles of rhodium), where COD is an abbreviation for 1,5-cyclooctadiene and CAMP is an abbreviation for cyclohexylanisylmethylphosphine, and the mixture is stirred. After 30 minutes 3.6 g of NaBPh₄(10.5 mmoles) is added and the suspension again is stirred for 30 minutes. The fine yellow precipitate is washed with ether and dried. The product is Rh(COD)(CAMP)$_2$BPh$_4$ as determined by elemental analysis.

A solution of 100 ml of acetone containing Rh(COD)(CAMP)$_2$ BPh$_4$ (10 mmoles) is treated with excess CO and concentrated to a volume of 10 ml. Crystallization from the acetone is accomplished by the addition of ethanol. The product is filtered and washed with ether in a CO atmosphere. The isolated compound is Rh(CO)$_3$(CAMP)$_2$BPh$_4$ as demonstrated by elemental analysis, ir, conductivity, and nmr data.

EXAMPLE 4

Two coordination complexes used for asymmetric hydroformylation of olefins, specifically RhClCO(optically active ligand)$_2$ and Rh(O$_2$CCH$_3$)CO (optically active ligand)$_2$ are prepared in situ by the addition of the optically active ligand (for example phenylanisylmethylphosphine, called PAMP) to a solution of (RhCl(CO)$_2$)$_2$ and (Rh(O$_2$CCH$_3$)(CO)$_2$)$_2$, respectively.

EXAMPLES 5-12

Examples 5-12 are representative of olefin hydroformylation using catalysts containing optically inactive ligands. The catalysts are similar in structure to the catalysts of the present invention with the single exception that they do not employ an optically active ligand. At least one of the products of each example in Table 1 has an asymmetric carbon atom and is consequently chiral. However, none of the products from any of these examples are optically active.

When these same olefins (also called feedstock or substrates) are hydroformylated using a catalyst with an optically active ligand (e.g., Rh(COD)(CAMP)$_2$BF$_4$ or Rh(NBD)(diop)BPh$_4$), the chiral product is optically active (see Tables 2-5). Specifically, compare the hydroformylation of vinyl acetate using an achiral catalyst (Example 5) with a similar experiment using an optically active catalyst (Example 13): in the latter case the product exhibits optical activity. A similar result is observed by comparing the hydroformylation of alpha-methyl styrene using an optically inactive catalyst (Example 9) with the results obtained employing an optically active catalyst (Example 27).

Example 5 is described in detail, while the remaining examples employ the general procedure of Example 5 with variations of catalyst systems, reaction conditions, and olefin substrates as noted in the tables.

EXAMPLE 5

A 300 ml batch reactor is charged with 0.1 mmoles of Rh(CO)$_3$(Ph$_3$P)$_2$BPh$_4$. (Ph=C$_6$H$_5$=phenyl). The reaction solvent benzene (100 ml) is added to the reactor which is then closed and flushed three times with the CO/H$_2$ gas blend (mole ratio 1 to 1). (If an excess of ligand is desired for complex stability or increased product selectivity, it is added before the autoclave is closed). The reactor and contents are heated to 100° C. under about 150 psig of CO/H$_2$. The reaction is started by injecting vinyl acetate (0.2 mole) into the reactor and raising the CO/H$_2$ pressure to 500 psig. This reactor pressure is maintained by continuously feeding CO/H$_2$ gas blend from a high-pressure reservoir of precisely known volume via a regulator. The number of moles of gas reacted is calculated from the pressure drop and volume of the reservoir. The rate of reaction is obtained by plotting the pressure of the reservoir as a function of time. When the reaction is complete (i.e., when the reservoir pressure does not change with time) the reactor and contents are cooled and the product solution analyzed by gas chromatography.

The product is separated and isolated by distillation at 63°-65° C. (35 mm) after first removing the solvent by distillation at atmospheric pressure. Under the general conditions of the present hydroformylation reaction, olefins and aldehyde are not appreciably hydrogenated to paraffins and alcohols respectively.

The pure alpha-acetoxypropionaldehyde (0.413 g) is dissolved in toluene and the solution diluted to 10.0 ml. The optical rotation of this solution is determined using a Perkin-Elmer 141 polarimeter. No optical activity is observed for any products obtained in examples 5 through 12.

EXAMPLES 13-19

Examples of the asymmetric hydroformylation of a specific olefin, vinyl acetate, are summarized in Table 2. The general procedure for hydroformylation, product separation, and optical rotation determination is that employed for example 5. The product in every example is alpha-acetoxypropionaldehyde in substantially 100% yield.

EXAMPLES 20-24

The examples summarized in Table 3 illustrate the asymmetric hydroformylation of styrene to the optically active chiral aldehyde alpha-phenylpropionaldehyde, used as a fragrance, for example at 0.1% to 10% in canine repellents. This compound designated as A is present with minor amounts of the achiral betaphenylpropionaldehyde, designated as B in Table 3.

The reaction solvent from the product solutions obtained in examples 20-24 is removed by distillation at atmospheric pressure. The product is recovered by distillation at 78° C. (9 mm of Hg). Optical rotations are determined as in Example 5.

EXAMPLES 25-27

Numerous other olefins can be hydroformylated to chiral products. The examples in Table 4 illustrate the process of this invention as applied to several other olefins. The detailed procedure is similar to that in example 5.

EXAMPLES 28-33

These examples show the use of other optically active ligands and other catalyst formulations including an iridium complex. The products observed are the same as previously described: Styrene is converted to the chiral alpha-phenylpropionaldehyde (designated as A) and the achiral beta-phenylpropionaldehyde (designated as B); Vinyl acetate is hydroformylated to alpha-acetoxpropionaldehyde (designated as C) in substantially 100% yield.

Solutions of cobalt complexes prepared in situ from Co$_2$(CO)$_8$ and the optically active CAMP ligand are also effective in the preparation of optically active products. Complexes containing non-coordinating anions other than BPh$_4$$^-$, namely ClO$_4$$^-$, BF$_4$$^-$, NO$_3$$^-$, PF$_6$$^-$, similarly result in optically active hydroformylation products. In other experiments the use of similar complexes employing optically active anions such as lactate and glutamate gives optically active products.

TABLE 1

| Example | Olefin | Products (yields %)[1] | | Complex mmoles | Temp. °C. / Press. psig |
|---|---|---|---|---|---|
| 5 | $CH_2=CHOCCH_3$ (vinyl acetate), $C=O$ | $CH_3\overset{O-C-CH_3}{\underset{CHO}{C}}-H$ | chiral (100) | $Rh(CO)_3(Ph_3P)_2BPh_4$ 0.1 | 100° 500 |
| 6 | $C_6H_5-CH=CH_2$ styrene | $C_6H_5-\overset{H}{\underset{CHO}{C}}-CH_3$ | chiral (88) | $RhHCO(Ph_3P)_3$ 0.1 | 80° 120 |
|  |  | $C_6H_5-C_2H_4-CHO$ | (12) |  |  |
| 7 | $CH_3-CH=CH-C_3H_7$ cis-2-hexene | $CH_3-\underset{CHO}{\overset{|}{C}H}-C_4H_9$ | chiral (84) | $Rh(COD)(Ph_3P)_2BF_4$ 0.1 | 100° 500 |
|  |  | $CH_3-CH_2-\underset{C_3H_7}{\overset{CHO}{\underset{|}{C}H}}$ | chiral (16) |  |  |
| 8 | $CH_3-CH=CH-C_2H_5$ cis-2-pentene | $CH_3-\underset{CHO}{\overset{|}{C}H}-C_3H_7$ | chiral (72) | $Rh(COD)(Ph_3P)_2BPh_4$ 0.1 | 80° 120 |
|  |  | $C_2H_5\underset{C_2H_5}{\overset{CHO}{\underset{|}{C}}}$ | (28) |  |  |
| 9 | $C_6H_5-\underset{CH_3}{\overset{|}{C}}=CH_2$ alpha-methyl styrene | $C_6H_5-\underset{CHO}{\overset{CH_3}{\underset{|}{C}}}-CH_3$ | (5) | $Rh(CO)_3(Ph_3P)_2BPh_4$ 0.5 | 125° 500 |
|  |  | $C_6H_5-\underset{H}{\overset{CH_3}{\underset{|}{C}}}-CH_2-CHO$ | chiral (95) |  |  |
| 10 | $CH_2=CH-\overset{O}{\underset{}{C}}OC_2H_5$ ethyl acrylate | $CH_3-\underset{CHO}{\overset{H}{\underset{|}{C}}}-\overset{O}{\underset{}{C}}-OC_2H_5$ | chiral (67) | $Rh(COD)(Ph_3P)_2BPh_4$ 0.5 | 100° 500 |
|  |  | $OHC-CH_2-CH_2-\overset{O}{\underset{}{C}}-OC_2H_5$ | (33) |  |  |
| 11 | $CH_2=CH-O-C_2H_5$ Ethyl vinyl ether | $CH_3-\underset{CHO}{\overset{|}{C}H}-O-C_2H_5$ | chiral (62) | $Rh(COD)(Ph_3P)_2BPh_4$ 0.5 | 125° 500 |
|  |  | $\underset{CHO}{CH_2-CH_2-O-C_2H_5}$ | (38) |  |  |
| 12 | $CH_2=CH-CH_2-O-C_2H_5$ Ethyl allyl ether | $CH_3-\underset{CHO}{\overset{|}{C}H}-CH_2-O-C_2H_5$ | chiral (30) | $Rh(COD)(Ph_3P)_2BPh_4$ 0.1 | 80° 120 |
|  |  | $CHO-C_3H_6-O-C_2H_5$ | (60) |  |  |

[1]Yields are mole percent based on reacted olefin

TABLE 2

| Example | Catalyst System[1] (mmole) | Specific Rotation $[\alpha]_D^{20}$ - degrees (Solvent, conc)[2] | Optical Purity % | Temp. °C. / Press. psig |
|---|---|---|---|---|
| 13 | Rh(COD)(CAMP)$_2$BPh$_4$ (0.5) CAMP (3.0) | +3.07 (neat) | 6.0 | 100° 500 |
| 14 | Rh(NBD)(CAMP)$_2$BF$_4$ (0.05) | +2.21 (neat) | 4.4 | 80° 120 |
| 15 | Rh(NBD)(diop)BPh$_4$ (0.1) | −7.61 (neat) | 15. | 60° 120 |
| 16 | Rh(COD)(diop)BPh$_4$ (0.1) diop (0.2) | −10.9 (toluene, C = 5.18) | 31. | 80° 120 |
| 17 | Rh(COD)(diop)BPh$_4$ (0.1) | −1.07 (toluene, C = 5.16) | 3.0 | 100° 1340 |
| 18 | Rh(COD)(diop) BPh$_4$ (0.1) | −4.09 (toluene, C = 5.53) | 11.6 | 80° 120 |
| 19 | Rh(COD)(diop)BPh$_4$ | −1.12 | 3.2 | 100° |

TABLE 2-continued

| Example | Catalyst System[1] (mmole) | Specific Rotation $[\alpha]_D^{20}$ - degrees (Solvent, conc)[2] | Optical Purity % | Temp. Press. °C. psig |
|---|---|---|---|---|
| | (0.1) | (toluene, C = 4.98) | | 120 |

[1]CAMP denotes cyclohexylanisylmethylphosphine and diop denotes levo-2,3,-O-isopropylidine-2,3,dihydroxy-1,4-bis(diphenylphosphino)butane.
[2]Concentration is reported in grams of sample per 100 ml of solution; neat means no solvent.

TABLE 3

| Example | Catalyst System (mmoles) | Product[1] (yield %) | Specific Rotation $[\alpha]_D^{20}$ - degrees (Solvent, conc)[2] | Optical Purity % | Temp. Press. °C. psig |
|---|---|---|---|---|---|
| 20 | Rh(COD)(CAMP)$_2$BF$_4$ (0.1) CAMP (1.3) | A (75) B (25) | +36.1 (toluene, C = 2.08) | 12.3 | 100° 120 |
| 21 | Rh(NBD)(CAMP)$_2$BF$_4$ (0.1) CAMP (1.0) | A (88) B (12) | +13.8 (toluene, C = 2.70) | 4.6 | 100° 500 |
| 22 | Rh(COD) (diop)BPh$_4$ (0.1) (diop) (0.2) | A (63) B (37) | −43.7 (toluene, C = 2.54) | 14.9 | 60° 120 |
| 23 | Rh(NBD) (diop)BPh$_4$ (0.1) | A (47) B (53) | −11.0 (toluene, C = 2.13) | 3.8 | 60° 120 |
| 24 | Rh(NBD) (diop)BF$_4$ (0.1) | A (58) B (42) | −1.6 (toluene, C = 2.48) | 0.54 | 80° 120 |

[1]Product yield based on reacted styrene, A is alpha-phenylpropionaldehyde, B is beta-phenylpropionaldehyde.
[2]Concentration is reported in grams of sample per 100 ml of solution.

TABLE 4

| Example | Catalyst System (mmole) | Temp. Press. °C. psig | Olefin and Product (yield %)[1] | | Specific Rotation $[\alpha]_D^{20}$ degrees (Solvent, conc)[2] |
|---|---|---|---|---|---|
| 25 | Rh(NBD)(CAMP)$_2$BF$_4$ 0.1 | 100° 500 | cis-2-hexene<br>CH$_3$—CH—C$_4$H$_9$<br>\|<br>CHO | (86) | 0.007 (neat) |
| | | | C$_2$H$_5$—CH—C$_3$H$_7$<br>\|<br>CHO | (14) | |
| 26 | Rh(COD)(diop)BPh$_4$ 0.1 | 80° 120 | cis-2-pentene<br>CH$_3$—CH—C$_3$H$_9$<br>\|<br>CHO | (44) | −0.035 (hexanal, C = 1.9) |
| | | | C$_2$H$_5$—CH—C$_2$H$_5$<br>\|<br>CHO | (19) | |
| 27 | Rh(NBD)(CAMP)$_2$BF$_4$ 1.3 CAMP 1.0 | 100° 500 | 2-methylstyrene<br>Ph—C(CH$_3$)(H)—CH$_2$—CHO | (92.) | −2.85 (toluene, C = 3.09) |
| | | | Ph—C(CH$_3$)$_2$—CHO | (8.) | |

[1]Product yield based on reacted olefin
[2]Concentration is reported in grams of sample per 100 ml of solution; neat means no solvent.

TABLE 5

| EXAMPLE | Catalyst System (mmole) | Olefin and Products (yield %)[1] | Specific Rotation $[\alpha]_D^{20}$ degree (Solvent, conc)[4] | Optical Purity % | Temp. Press. °C. psig |
|---|---|---|---|---|---|
| 28 | RhClCO(PAMP)$_2$[2] (0.1) | Styrene A (72) B (28) | 0.50 (toluene, C = 2.61) | 0.2 | 100° 500 |
| 29 | Rh$_4$(CO)$_{12}$ 0.025 | Styrene A (90) | 1.40 (toluene, C = 2.88) | | 100° 500 |

TABLE 5-continued

| EXAMPLE | Catalyst System (mmole) | Olefin and Products (yield %)[1] | Specific Rotation $[\alpha]_D^{20}$ degree (Solvent, conc)[4] | Optical Purity % | Temp. °C | Press. psig |
|---|---|---|---|---|---|---|
|  | PAMP[2] (0.2) | B (10) |  | 0.5 |  |  |
| 30 | Rh(OAc) (CO) (PAMP)$_2$[2] (0.1) | Styrene A (89) | 1.20 (toluene, C = 2.91) | 0.4 | 100° | 500 |
|  |  | B (11) |  |  |  |  |
| 31 | Rh(NBD) (Ph$_3$P)$_2$BPh$_4$ (0.1) | Styrene A (94) | 1.20 (toluene, C = 2.81) | 0.4 | 60° | 120 |
|  | PAMP[2] (0.6) | B (6) |  |  |  |  |
| 32 | (RhOAc(CO)$_2$)$_2$ (0.05) MBDP[3] (1.0) | vinyl acetate C (100) | 0.44 (toluene, C = 4.96) | 1.2 | 80° | 120 |
| 33 | Ir(CO)$_3$(Ph$_3$P)$_2$BPh$_4$ (0.1) diop (0.2) | vinyl acetate C (67) | −0.17° (toluene, C = 3.46) | 0.5 | 125° | 500 |

[1] A is alpha-phenylpropionaldehyde, B is beta-phenylpropionaldehyde, and C is alpha-acetoxypropionaldehyde.
[2] PAMP is phenylanisylmethylphosphine and OAc is acetate.
[3] MBDP is S-(+)-(2-Methylbutyl)diphenylphosphine.
[4] Concentration is reported in grams of sample per 100 ml of solution.

List of Olefins for Asymmetric Hydroformylation and Products:

| OLEFIN | PRODUCT |
|---|---|
| 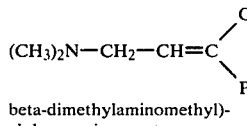<br>beta-dimethylaminomethyl)-alpha-propionoxystyrene | 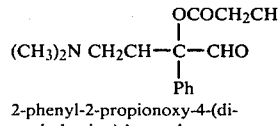<br>2-phenyl-2-propionoxy-4-(dimethylamino)-butanal |
| 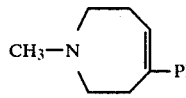<br>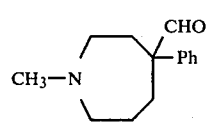<br>N-methyl-1-phenyl-5-aza-cycloheptene<br>N-methyl-1-phenyl-4-aza-cyclo heptene | 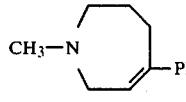<br>N-methyl-1-phenyl-4-azacyclo-heptanecarboxaldehyde |
| 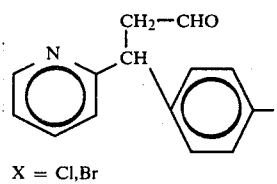<br>alpha-(2-pyridinyl)-4-halo-styrene<br>halo = chlorine, bromine | 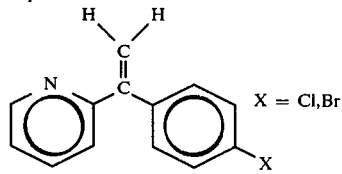<br>X = Cl, Br<br>3-(2-pyridinyl)-3-(4-halo-phenyl)-propanal<br>halo = chlorine, bromine |
| 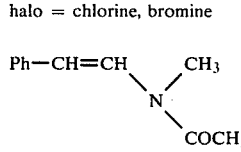<br>N-acetyl-beta-(methylamino)-styrene | 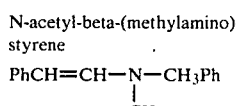<br>N-acetyl-2-(methylamino)-3-phenylpropanal |
| 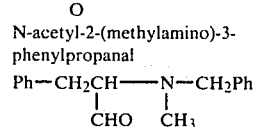<br>N-benzyl-beta-(methylamino) styrene | 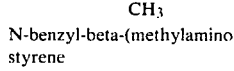<br>N-Benzyl- 2-(methylamino)-3-phenyl propanal. |

-continued
List of Olefins for Asymmetric Hydroformylation and Products:

| OLEFIN | PRODUCT |
|---|---|
| ![alpha-acetoxy-beta-cyclohexylidene styrene] Ph, OCOCH₃ on C=cyclohexylidene<br>alpha-acetoxy-beta-cyclohexylidene styrene | OCOCH₃ / Ph—C—CHO with cyclohexyl (S)<br>acetoxycyclohexylphenylacetaldehyde |
| Ph—CH=CH—CH₃<br>beta-methylstyrene | Ph—CH—CHO<br>\|<br>CH₂—CH₃<br>2-phenylbutanal |
| OCH=CH—OCOCH₃ on 1-naphthyl<br>1-acetoxy-2-(1-napthoxy)-ethylene | O—CH₂—CH—CHO<br>\|<br>OCOCH₃ on 1-naphthyl<br>2-acetoxy-3-(1-napthoxy)-propanal |
| CH₃O-cyclohexyl-OCH=CH—OCOCH₃<br>1-acetoxy-2-(ortho-methoxyphenoxy)-ethylene | OCOCH₃<br>\|<br>CH₃O-cyclohexyl-OCH₂—CH—CHO<br>2-acetoxy-3-(ortho-methoxyphenoxy)-propanal |
| 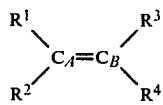<br>beta-(2-aza-cyclohexylidene) Styrene | 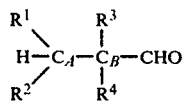<br>phenyl-(2-piperidyl)-acetaldehyde |
| Cl—C₆H₄—O—CH=CH—OCOCH₃<br>1-acetoxy-2-(para-chlorophenoxy)-ethylene | Cl—C₆H₄—CH₂CH—CHO<br>\|<br>OCOCH₃<br>2-acetoxy-3-(4-chlorophenoxy)-propanal |

What is claimed is:

1. A process for the conversion of prochiral olefins of the formula $$\begin{array}{c}R^1\\ \diagdown\\ R^2\end{array}C_A=C_B\begin{array}{c}R^3\\ \diagup\\ R^4\end{array}$$

to optically active aldehydes of the formula $$\begin{array}{c}R^1\\ \diagdown\\ R^2\end{array}H-C_A-C_B\begin{array}{c}R^3\\ |\\ R^4\end{array}-CHO$$

with the restrictions that
(I) $R^1$ is not identical to $R^2$; or
(II) $R^3$ is not identical to $R^4$; and furthermore,
(III) neither $R^1$ nor $R^2$ can be hydrogen; or
(IV) neither $R^3$ nor $R^4$ can be the formyl group (—CHO): and
$R^1$, $R^2$, $R^3$ and $R^4$ are each independently selected from the group consisting of (a) hydrogen (b) alkyl having at least one and a maximum of twenty-five carbon atoms (c) substituted alkyl said substitution being selected from the group consisting of amino, including alkylamino and dialkylamino, hydroxy, alkoxy, acyloxy, halo, nitro, nitrile, thio, carbonyl, carboxamide, carboxaldehyde, carboxyl, carboxylic ester said ester having a maximum of ten carbon atoms, (d) aryl including phenyl (e) substituted aryl including phenyl said substitution being selected from the group consisting of alkyl having a maximum of six carbon atoms, amino including alkylamino, hydroxy, alkoxy, acyloxy, halo, nitrile, nitro, carboxyl, carboxaldehyde, carboxylic ester, said ester having a maximum of ten carbon atoms, carbonyl, and thio, said aryl substitution being less than four substituents (f) acyloxy, (g) alkoxy, (h) amino including alkylamino and dialkylamino, (i) acylamino and diacylamino, (j) nitro (k) carbonyl (l) nitrile (m) carboxyl (n) carboxamide (o) carboxaldehyde (p) carboxylic ester said ester having a maximum of 10 carbon atoms (q) alkylmercapto, provided that the compound after hydroformulation is chiral, which comprises contacting said prochiral olefin with carbon monoxide and hydrogen at a total pressure of from 50 to 2000 psig, and at a temperature of from 25° C. to 180° C., in the presence of a catalyst system formed from a soluble metal component and optically active ligands where the metal is iridium.

2. A process for the conversion of prochiral olefins of the formula

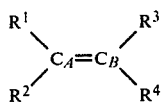

to optically active aldehydes of the formula

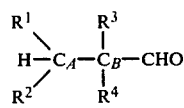

with the restrictions that
(I) $R^1$ is not identical to $R^2$; or
(II) $R^3$ is not identical to $R^4$; and furthermore,
(III) neither $R^1$ nor $R^2$ can be hydrogen; or
(IV) neither $R^3$ nor $R^4$ can be the formyl group (—CHO); and $R^1$, $R^2$, $R^3$ and $R^4$ are each independently selected from the group consisting of (a) hydrogen (b) alkyl having at least one and a maximum of twenty-five carbon atoms (c) substituted alkyl said substitution being selected from the group consisting of amino, including alkylamino and dialkylamino, hydroxy, alkoxy, acyloxy, halo, nitro, nitrile, thio, carbonyl, carboxamide, carboxaldehyde, carboxyl, carboxylic ester said ester having a maximum of ten carbon atoms, (d) aryl including phenyl (e) substituted aryl including phenyl said substitution being selected from the group consisting of alkyl having a maximum of six carbon atoms, amino including alkylamino, hydroxy, alkoxy, acyloxy, halo, nitrile, nitro, carboxyl, carboxaldehyde, carboxylic ester, said ester having a maximum of ten carbon atoms, carbonyl, and thio, said aryl substitution being less than four substituents (f) acyloxy, (g) alkoxy, (h) amino including alkylamino and dialkylamino, (i) acylamino and diacylamino, (j) nitro (k) carbonyl (l) nitrile (m) carboxyl (n) carboxamide (o) carboxaldehyde (p) carboxylic ester said ester having a maximum of 10 carbon atoms (q) alkylmercapto, provided that the compound after hydroformylation is chiral, which comprises contacting said prochiral olefin with carbon monoxide and hydrogen at a total pressure of from 50 to 2000 psig, and at a temperature of from 25° C. to 180° C., in the presence of a catalyst provided by $M(An)_w(olefin)_x(CO)_y(L^*)_z$ where M is iridium; (An) is a coordinating or noncoordinating anion; $L^*$ is an optically active ligand and w, x, y, and z are whole numbers from 0 to 4, and $w+x+y+z$ is 4, 5, or 6.

* * * * *